United States Patent
Monaghan et al.

(10) Patent No.: US 10,861,175 B1
(45) Date of Patent: Dec. 8, 2020

(54) SYSTEMS AND METHODS FOR AUTOMATIC DETECTION AND QUANTIFICATION OF POINT CLOUD VARIANCE

(71) Applicant: Illuscio, Inc., Culver City, CA (US)

(72) Inventors: Robert Monaghan, Ventura, CA (US); Joseph Bogacz, Perth (CA)

(73) Assignee: Illuscio, Inc., Culver City, CA (US)

( * ) Notice: Subject to any disclaimer, the term of this patent is extended or adjusted under 35 U.S.C. 154(b) by 0 days.

(21) Appl. No.: 15/929,950

(22) Filed: May 29, 2020

(51) Int. Cl.
| | | |
|---|---|---|
| *G06T 7/33* | (2017.01) | |
| *G06T 7/38* | (2017.01) | |
| *G16H 50/80* | (2018.01) | |
| *G16H 70/60* | (2018.01) | |
| *G06K 9/62* | (2006.01) | |

(52) U.S. Cl.
CPC ........... *G06T 7/344* (2017.01); *G06K 9/6211* (2013.01); *G06T 7/38* (2017.01); *G16H 50/80* (2018.01); *G16H 70/60* (2018.01)

(58) Field of Classification Search
CPC .......... G06K 9/6211; G06K 9/46; G06K 9/62; G06K 2009/6213; G06T 7/33; G06T 7/344; G06T 7/38
USPC ........ 382/154, 151, 293–294, 100, 103–104, 382/106–107, 113
See application file for complete search history.

(56) References Cited

U.S. PATENT DOCUMENTS

| | | | | |
|---|---|---|---|---|
| 10,614,579 | B1 * | 4/2020 | Kwon | G06K 9/00214 |
| 2008/0246759 | A1 * | 10/2008 | Summers | G06T 17/00 |
| | | | | 345/420 |
| 2010/0310154 | A1 * | 12/2010 | Barrois | G06T 7/593 |
| | | | | 382/154 |
| 2015/0098645 | A1 * | 4/2015 | Leung | G06F 16/786 |
| | | | | 382/154 |
| 2017/0154436 | A1 * | 6/2017 | Zhang | G06T 7/593 |
| 2017/0299404 | A1 * | 10/2017 | Wang | G06T 7/80 |
| 2019/0026920 | A1 * | 1/2019 | Yi | G06T 7/74 |
| 2019/0286915 | A1 * | 9/2019 | Patil | G06T 7/73 |

* cited by examiner

*Primary Examiner* — Dwayne D Bost
*Assistant Examiner* — Stephen M Brinich
(74) *Attorney, Agent, or Firm* — Ansari Katiraei LLP; Arman Katiraei; Sadiq Ansari

(57) ABSTRACT

A comparator may automatically detect and quantify subtle and/or microscopic variance to a feature of a three-dimensional ("3D") object in a reproducible manner based on point cloud imaging of that 3D object. The comparator may isolate a first set of data points, that represent the object feature at a first time, in a reference point cloud, and may isolate a second set of data points, that represent the same but altered object feature at a different second time, in a non-reference point cloud. The comparator may detect variance between positional values and visual characteristic values of the second set of data points and the corresponding positional values and visual characteristic values of the first set of data points, and may quantify a change occurring to the object feature between the first time and the second time based on a mapping of the variance to a particular unit of measure.

20 Claims, 10 Drawing Sheets

US 10,861,175 B1

SYSTEMS AND METHODS FOR AUTOMATIC DETECTION AND QUANTIFICATION OF POINT CLOUD VARIANCE

BACKGROUND

Many industries have a need to detect subtle or microscopic changes in a three-dimensional ("3D") object. This need may be addressed by trained professionals that examine images of the object in order to ascertain if the object has changed in the different images. Such manual detection is subject to variability, inaccuracy, and subjectivity, especially when the changes being detected are subtle or microscopic, and/or when the object itself is subject to change as is the case when examining living organisms. Missed or inaccurate detection of the changes can have significant ramifications in many industries including agricultural, structural engineering, science, medicine, and/or archeology.

DETAILED DESCRIPTION OF PREFERRED EMBODIMENTS

The following detailed description refers to the accompanying drawings. The same reference numbers in different drawings may identify the same or similar elements.

Provided are systems and methods for automatically detecting and quantifying variance to a particular feature of a three-dimensional ("3D") object based on point cloud imaging of that 3D object. In some embodiments, a point cloud comparator may be implemented to objectively and consistently detect and quantify the changes to the particular feature in the point clouds, thereby providing accurate results for subtle and even microscopic changes that would be undetected by the human eye.

The point cloud comparator may programmatically isolate the particular feature within a three-dimensional ("3D") object by aligning different point clouds that image the 3D object. The point cloud comparator may align the different point clouds by locating sets of data points with similar data elements that represent one or more of the same landmarks about the periphery or exterior of each point cloud. The point cloud comparator may then locate the particular feature by traversing similar internal landmarks that lead to the particular feature of interest in the different point clouds despite data points for one or more of the 3D object, landmarks, or the particular feature changing over time. The point cloud comparator may perform a machine analysis of the data points that represent the particular feature in the different aligned point clouds, and may accurately determine and quantify subtle and/or microscopic changes to the particular feature based on the machine analysis.

Figure 1:
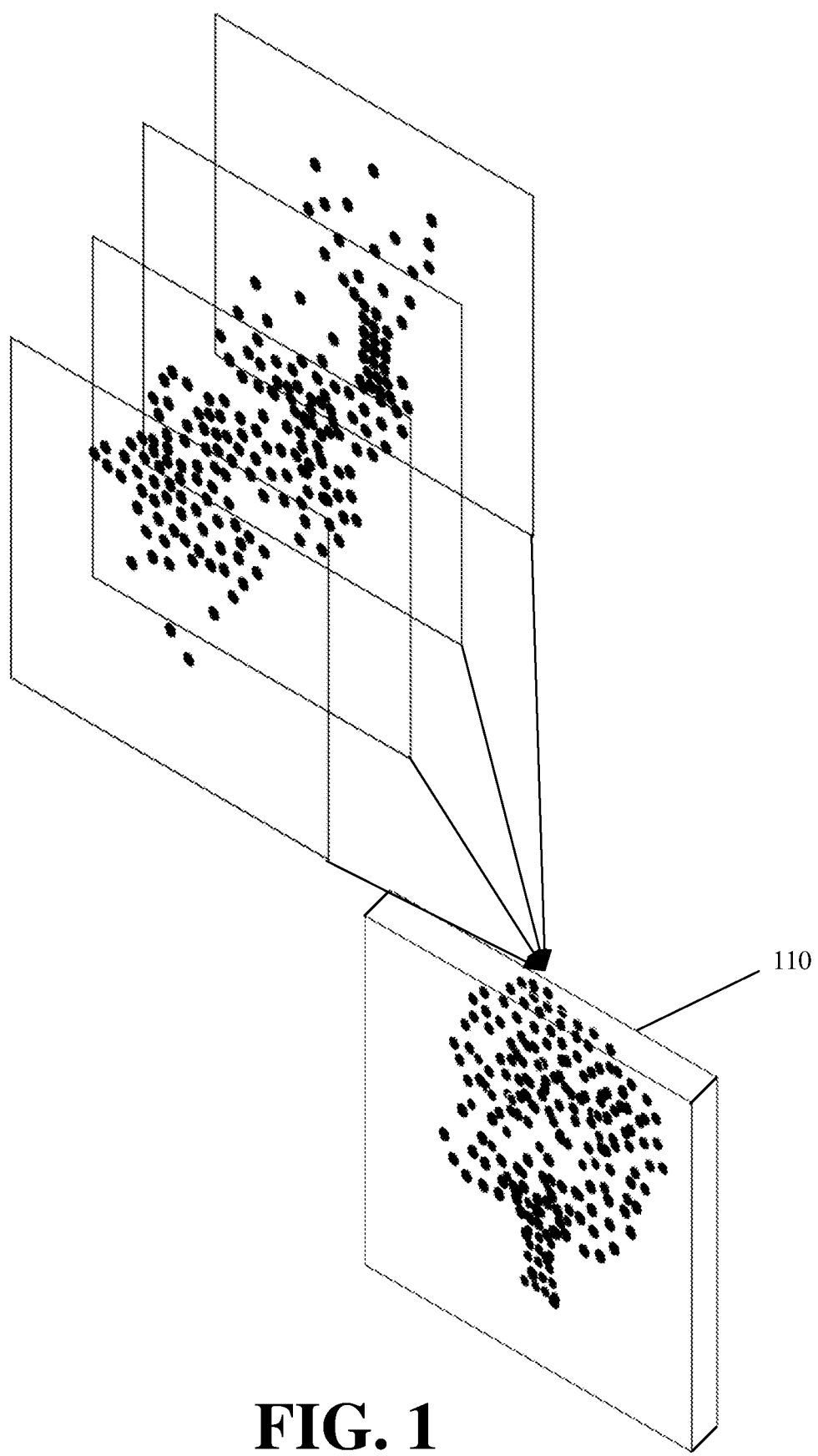
FIG. 1 illustrates an example point cloud that represents a three-dimensional ("3D") object using data points with different visual characteristics at different 3D positions.

A point cloud may include a set of data points for representing a 3D or volumetric object. FIG. 1 illustrates an example point cloud 110 that represents a 3D object using data points with different visual characteristics at different 3D positions.

The point cloud data points may differ from pixels of a two-dimensional ("2D") image, because certain regions of the point cloud may have no data points, lower densities of data points, and/or higher densities of data points based on varying amounts of visual information that is detected at those regions. In contrast, pixels of a 2D image have a uniform density and fixed arrangement that is defined by the resolution of the 2D image. Moreover, the point cloud data points may have a non-uniform placement or positioning, whereas the 2D image has pixel data for each pixel of a defined resolution (e.g., 640×480, 800×600, etc.).

Each point cloud data point or set of data points may correspond to a different feature of the 3D object, and each feature may be microscopic in size and difficult to detect with the human eye. Each point cloud data point may include positional and non-positional information.

The positional information may include coordinates within 3D space. For instance, each point cloud data point may include x-coordinate, y-coordinate, and z-coordinate data point elements for each imaged feature of the 3D object.

The non-positional data point elements may include information about the visual characteristics of the imaged feature. The visual characteristics may correspond to a detected color. The color may be represented using red, green, and blue ("RGB") values. In some embodiments, the visual characteristics may provide the chrominance and/or luminance of the imaged feature. In some other embodiments, the visual characteristics may be related to properties of the imaging device used to capture the object feature at a particular data point. For instance, the visual characteristics may include a Tesla strength value to quantify the strength of the magnetic field that was used in detecting and/or imaging the object part. In some embodiments, the non-positional data elements may include energy, audible or sound, and/or other characteristics of the imaging device or the object being imaged. Accordingly, the non-positional data element can include any property of the imaged object part (e.g., hue, saturation, brightness, reflectivity, etc.) or of the imaging device used to capture the object part at a corresponding data point in 3D space.

Each point cloud data point may include an array of data elements. The array of data elements may provide the positioning of the data point in 3D space as well as one or more visual characteristics of that data point. For instance, a point cloud data point may be stored and/or represented as an array of data elements with some combination of x-coordinate, y-coordinate, z-coordinate, red, green, blue, chrominance, luminance, tesla, and/or other values. The point cloud data points and the values of their corresponding data elements may be generated by a 3D or depth-sensing camera, Light Detection and Ranging ("LiDAR"), Magnetic Resonance Imaging ("MRI") devices, Positron Emission Tomography ("PET") scanning devices, Computerized Tomography ("CT") scanning devices, time-of-flight devices, and/or other imaging equipment.

Small deviations in the number of data points representing a particular feature or the arrangement of those features may be challenging to detect with the human eye. Moreover, the particular feature and/or other surrounding features of the same object may change in any of three dimensions over time when the point cloud is representative of a living organism (e.g., a cell or part of a plant, animal, human, or other living object) or an object that is subject to decay or other change (e.g., an object that changes shape in response to temperature changes, light, etc.).

Figure 2:
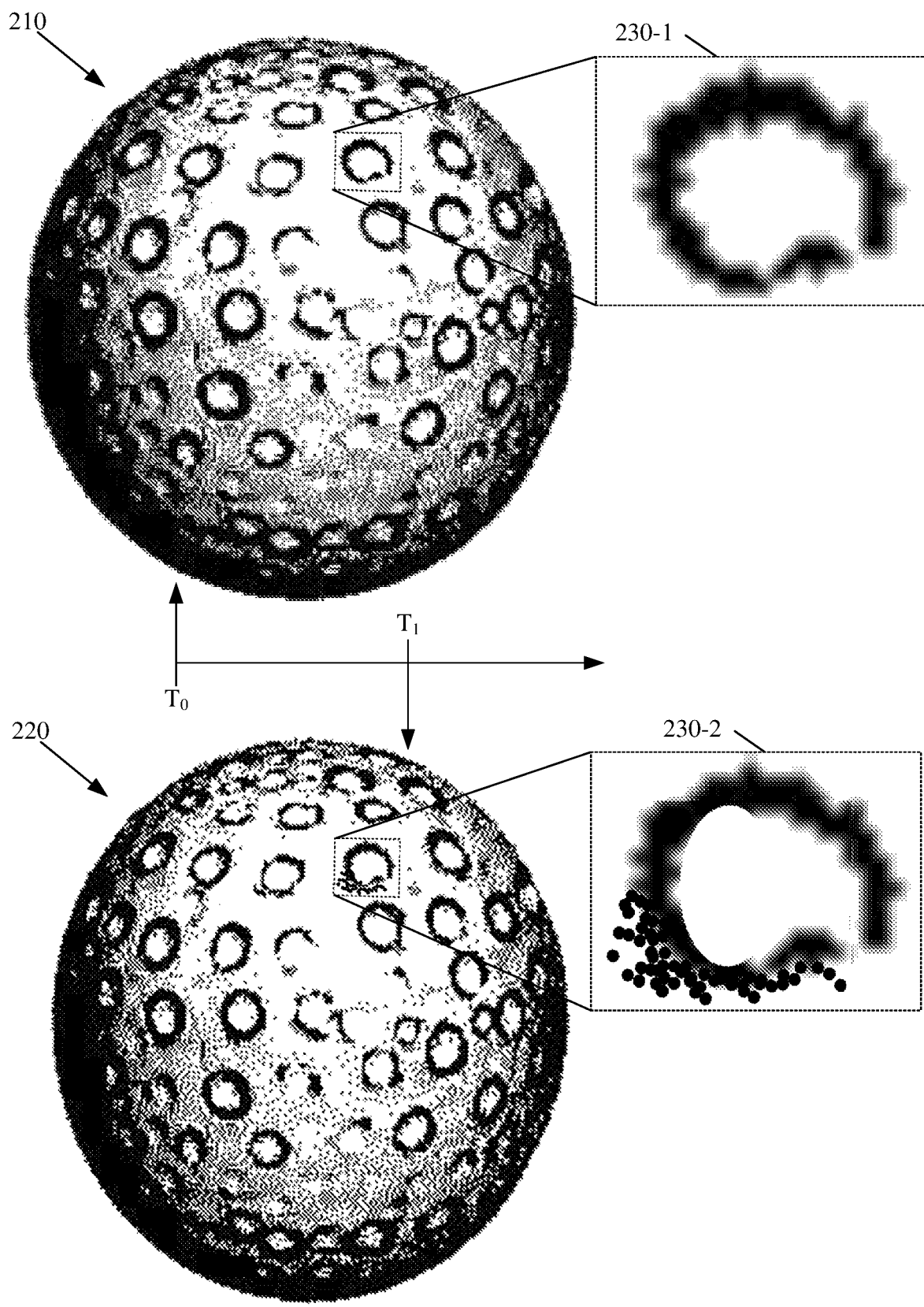
FIG. 2 illustrates an example of two different point clouds that present the same object at different times in accordance with some embodiments presented herein.

FIG. 2 illustrates an example of two different point clouds 210 and 220 that present the same object at different times in accordance with some embodiments presented herein. An imaging device may produce first point cloud 210 for the object at a first time, and may produce second point cloud 220 for the object at a later second time. First point cloud 210 and second point cloud 220 may provide a 3D rendering or image of the object. In some embodiments, first point cloud 210 and second point cloud 220 may be deconstructed to illustrate subsets of data points at each layer, plane, or z-coordinate depth. For instance, the point cloud comparator, imaging device, and/or another device rendering point clouds 210 and 220 may zoom into and out of point clouds 210 and 220 to view the surface or periphery of the object at different distances and/or to view internal features of the object that are captured at different z-depths or planes. In some embodiments, point clouds 210 and 220 may be rotated, tilted, and/or otherwise manipulated in order to obtain different perspectives or views of the object exterior and interior.

Second point cloud 220 may be slightly skewed relative to first point cloud 210 due to a change in the object's position relative to the imaging device after first point cloud 210 is produced and before second point cloud 220 is produced. The movement may be organic and due to the object changing shape, size, or other physical properties over time. The movement may be due to impact to the object or the imaging device. The skew may cause second point cloud 220 to be misaligned with first point cloud 210, thereby making a direct comparison of point clouds 210 and 220 more challenging to a human observer. In some embodiments, the misalignment may be due to tolerances or imprecision of the imaging device when generating first point cloud 210 and second point cloud 220.

Even if there is no misalignment or the misalignment is corrected, first point cloud 210 and second point cloud 220 may appear similar to the human eye. However, as shown in the zoomed-in views of particular feature 230-1 from first point cloud 210 and the same particular feature 230-2 from second point cloud 220 (sometimes collectively referred to as "particular features 230" or individually as "particular feature 230"), there may be a higher concentration of data points for particular feature 230-2 of the object in second point cloud 220 than in first point cloud 210. This change in point clouds 210 and 220 may be subtle or microscopic in scale, but may have a significant impact to the object. For instance, the change to particular feature 230 may represent an undesired or desired growth, a viral spread, increased inflammation, and/or a repaired or healed feature. Other subtle or microscopic changes may be captured via differences in the visual characteristics of the data points representing particular feature 230. In some embodiments, there may be no difference in the number or positioning of the data points from first point cloud 210 and second point cloud 220. However, in some such embodiments, the microscopic or subtle difference may manifest via changes in the visual characteristics of the data points.

The point cloud comparator may compare the data points of first point cloud 210 against the data points of second point cloud 220 to detect the change to particular feature 230, and may quantify the change by measuring the change in size, shape, form, density, and/or physical properties of particular feature 230.

The point cloud comparator may be used in several different industries where detecting and quantifying these feature changes or changes under the surface of an object are of value. For instance, the point cloud comparator may be used in agriculture to determine whether fruit, vegetables, plants, trees, and/or agricultural products are disease-free, are growing correctly, have begun to rot, have reached peak ripeness, etc. The point cloud comparator may be used in manufacturing to compare manufactured goods against an original master and/or to determine quality of each manufactured good. The point cloud comparator may be used by artists, dealers, purchasers, and/or inspectors to distinguish original from fakes, reproductions, or forgeries of the original. The point cloud comparator may be used by scientists to determine molecular compositions, stability, bonding, reactions, etc. The point cloud comparator may be used by archaeologists to measure decay in artifacts and/or to date the artifacts. The point cloud comparator may be used by engineers to determine effects of pressure, weight, magnetism, speed, time, and/or other forces on objects as well as to measure the structural integrity of materials. The point cloud comparator may be used by clinicians and doctors to detect and/or measure spread of viruses, bacteria, cancers, tumors, and/or foreign elements in a body, the reaction of the body to the foreign elements, and/or a patient's health and/or recovery. For instance, the point cloud comparator, via the automatic variance detection and quantification, may detect an increase or decrease in T-cell counts, white blood cell counts, antibodies, inflammation, and/or other masses (e.g., bone growth or density) as well as recovery after surgical procedures.

In some embodiments, the point cloud comparator may align the different point clouds of the same object before performing the variance detection and quantification. The point cloud alignment may correct for any shifts to the object and/or the point cloud data points that occur because of the imaging equipment or positioning of the object, rather than changes to the object itself. For instance, an imaging device may produce different point clouds for a particular object over the span of several weeks. Each time a point cloud is generated, the particular object may be located at a slightly different position or orientation relative to the imaging device. Even a millimeter worth of misalignment may skew the variance detection and quantification results when the sought-after variances are subtle or microscopic in scope. By aligning the point clouds before performing the variance detection and quantification, the point cloud comparator may ensure that the detected and quantified variance is the result of changes occurring to or within the object rather than external factors that could otherwise bias or distort a direct comparison of the same feature in different point clouds.

The point cloud comparator may perform the alignment relative to one of a plurality of different point clouds that is designated as a reference point cloud. In other words, the point cloud comparator may align the other point clouds of the plurality of different point clouds, that represent different scans or images of the same object, to the point cloud that is selected as the reference point cloud.

The reference point cloud selection may further include keying the variance detection and quantification to at least one particular feature of the reference point cloud. The selection of the particular feature may reduce the computational overhead associated with the variance detection and quantification as point cloud comparator can focus the variance detection and quantification to a subset of data points in different point clouds that represent the particular feature of interest rather than scan for any and all variance across millions of data points that represent each feature of the imaged 3D object.

Figure 3:
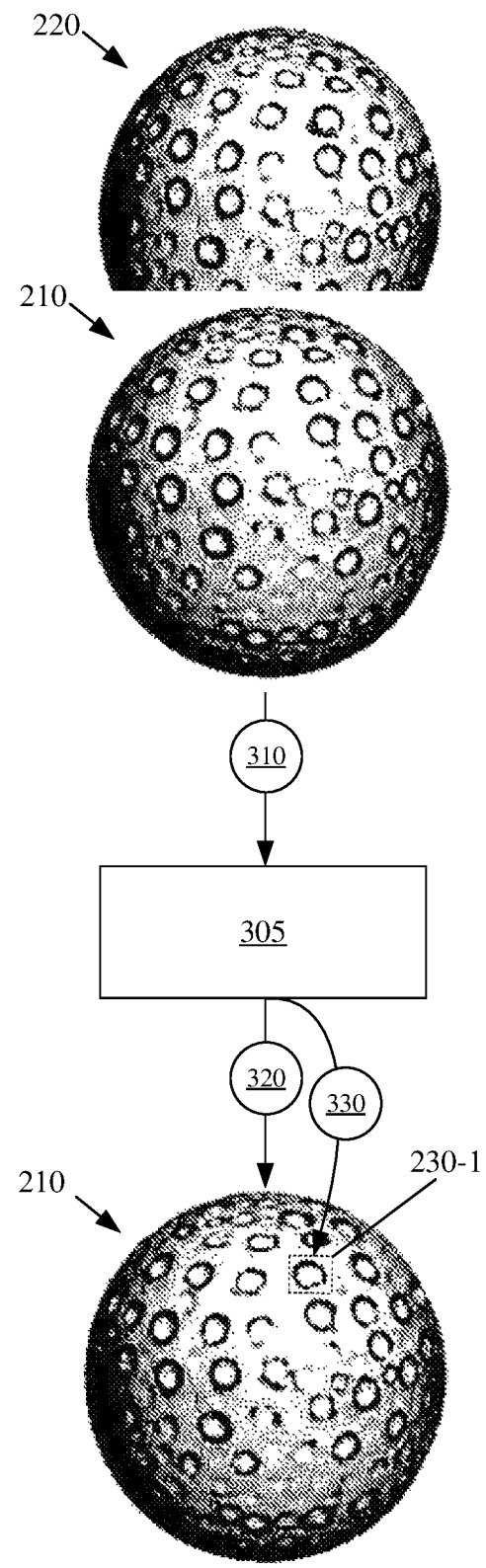
FIG. 3 illustrates an example for keying the variance detection and quantification off a reference point cloud and a particular feature of the reference point cloud in accordance with some embodiments presented herein.

FIG. 3 illustrates an example for keying the variance detection and quantification off a reference point cloud and a particular feature of the reference point cloud in accordance with some embodiments presented herein. As shown in FIG. 3, point cloud comparator 305 may receive (at 310) at least first point cloud 210 and second point cloud 220. First point cloud 210 and second point cloud 220 may be of a time series or different scans that capture the same object at different times via different point clouds with 3D sets of data points.

Point cloud comparator 305 may select and/or designate (at 320) first point cloud 210 as the reference point cloud. Point cloud comparator 305 may align other point clouds (e.g., second point cloud 220 and a third point cloud for the same object) relative to the reference point cloud (e.g., first point cloud 210) so that the same feature can be identified in the different point clouds of the same object, and so that accurate comparisons can be made of the feature in the different point clouds from a common point of reference (e.g., alignment, orientation, positioning, etc.).

In some embodiments, point cloud comparator 305 may automatically select (at 320) first point cloud 210 as the reference point cloud against which second point cloud 220 is to be aligned. The reference point cloud can be any point cloud in a sequence of point clouds of the same object. In some embodiments, the reference point cloud may be the earliest or first point cloud in the sequence of point clouds (e.g., earliest timestamp).

Point cloud comparator 305 may isolate (at 330) particular feature 230-1 in the reference point cloud to become the target of the feature variance detection. Particular feature 230-1 may correspond to a region of interest or a set of data points within the reference point cloud. The region of interest may be a specific part of the imaged object that is of interest or where change is to be measured. For instance, the region of interest may correspond to a set of data points that represent a cancerous growth on an organ, a diseased area on an organism, an infected part of an organism, a segment with quality control issues, an area at which a forgery, fake, or copy can be distinguished from an original, and/or an area where decay, rot, or other change has started or is monitored on an object.

To isolate (at 330) particular feature 230-1, point cloud comparator 305 may receive input with which particular feature 230 may be automatically identified in first point cloud 210 by point cloud comparator 305. For instance, point cloud comparator 305 may receive input that requests identification of a cancerous growth, a diseased area on an organism, an infected part of an organism, and/or an area where decay, rot, or other change has started or is monitored on an object. Point cloud comparator 305 may compare data points of the reference point cloud to data points of a baseline set of point clouds that capture the same or similar objects, and may detect the region or set of data points for particular feature 230-1 based on a detected difference between the region of the reference point cloud and the same region in the baseline set of point clouds. For instance, the baseline set of point clouds may correspond to scans of a healthy organ from different patients, and the reference point cloud (e.g., first point cloud 210) may be a scan of the same organ but with an abnormal growth, infection, disease, inflammation, or other change at the region that becomes the particular feature 230-1 of interest.

In some embodiments, particular feature 230-1 may be manually identified. For instance, a user may select a region or a set of data points in the reference point cloud as particular feature 230-1 of interest, and point cloud comparator 305 may store or reference the selection for subsequent variance detection and quantification.

Figure 4:
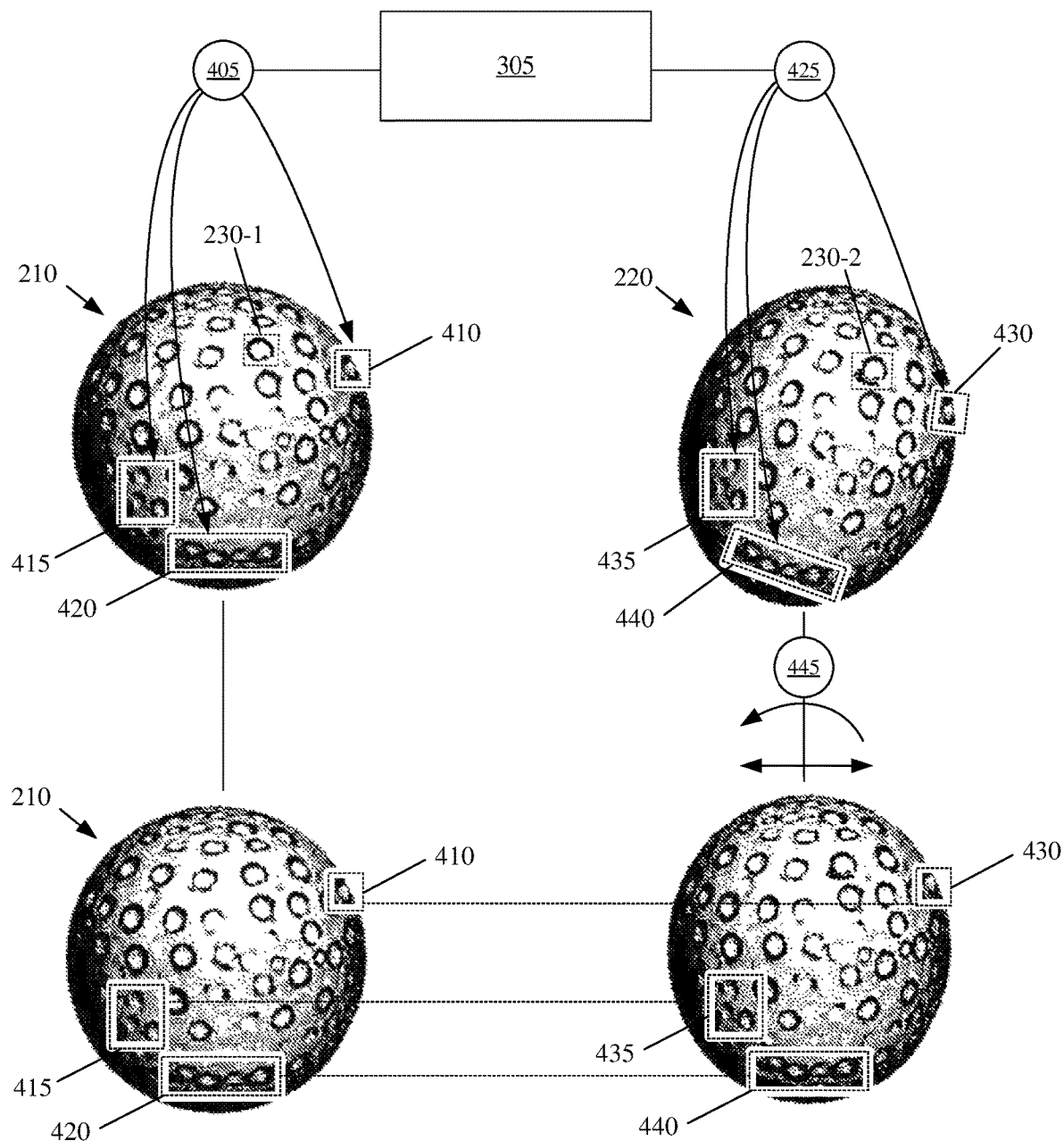
FIG. 4 illustrates an example by which a point cloud comparator may align different point clouds of the same object based on the reference point cloud in accordance with some embodiments presented herein.

Point cloud comparator 305 may then use the reference point cloud to align other point clouds that are produced for the same object represented by the reference point cloud, and to perform a direct and aligned comparison of particular feature 230 across the point clouds. FIG. 4 illustrates an example by which point cloud comparator 305 may align different point clouds of the same object based on the reference point cloud in accordance with some embodiments presented herein. In FIG. 4, first point cloud 210 may be selected as the reference point cloud, and point cloud comparator 305 may align second point cloud 220 relative to first point cloud 210.

To align point clouds 210 and 220, point cloud comparator 305 may determine the periphery of the reference point cloud (e.g., first point cloud 210). For instance, point cloud comparator 305 may identify the outermost point cloud data points that correspond to the outer edges or surface of the larger object that is represented by first point cloud 210. Point cloud comparator 305 may then identify (at 405) unique landmarks 410, 415, and 420 at the periphery. Landmarks 410, 415, and 420 may correspond to a distinctive grouping or clustering of data points that deviate from a pattern or placement of other data points at the outer edges. Landmarks 410, 415, and 420 may correspond to static or unique formations about the periphery of point clouds 210 and 220 from which point cloud comparator 305 may determine the orientation, positioning, and/or layout of point clouds 210 and 220 relative to one another.

Point cloud comparator 305 may scan the data points at the periphery (e.g., at the outer edges or surface) of second point cloud 220 to identify (at 425) clusters of data points 430, 435, and 440 that correspond to landmarks 410, 415, and 420 respectively. Once data points 430, 435, and 440 corresponding to landmarks 410, 415, and 420 are located on the periphery of second point cloud 220, point cloud comparator 305 may align (at 445) second point cloud 220 with first point cloud 210.

Aligning (at 445) point clouds 210 and 220 may include computing an offset between clusters of data points 430, 435, and 440 and landmarks 410, 415, and 420, and/or rotating, reorienting, shifting, and/or otherwise repositioning second point cloud 220 relative to first point cloud 210 so that clusters of data points 430, 435, and 440 become aligned to landmarks 410, 415, and 420 by at least a threshold amount. In some embodiments, aligning (at 445) second point cloud 220 relative to first point cloud 210 may involve changing the relative positioning of the data points without changing the actual coordinates of the point cloud data points. In some other embodiments, aligning (at 445) second point cloud 220 relative to first point cloud 210 may involve performing a common adjustment to data points of second point cloud 220. For instance, all data points of second point cloud 220 may have their x-coordinate elements reduced by a first value and their y-coordinate elements increased by a second value.

The alignment may correct for different positions, angles, heights, and/or properties at which the data points of the different point clouds 210 and 220 are captured and/or generated. The alignment may not correct for any changes that occur to the object in between the time first point cloud 210 and second point cloud 220 are captured and/or generated.

Figure 5:
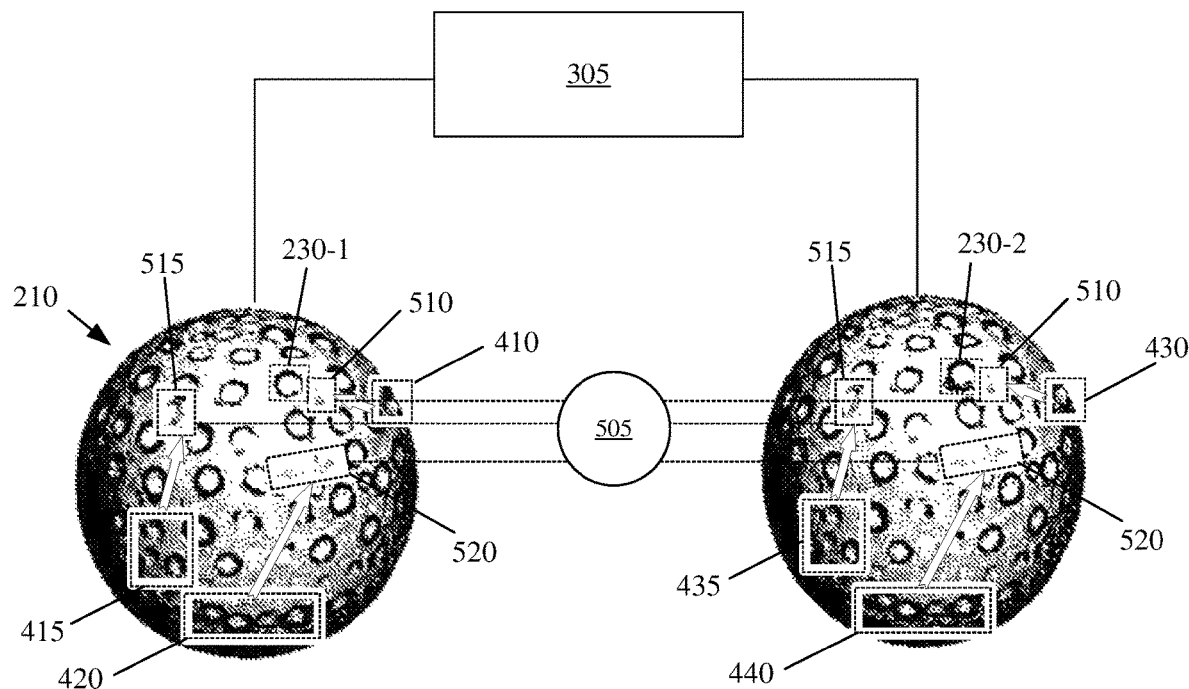
FIG. 5 illustrates an example of feature isolation performed by the point cloud comparator in accordance with some embodiments presented herein.

Point cloud comparator 305 may isolate particular feature 230-2 in second cloud point 220 once second point cloud 220 is aligned with first point cloud 210 and first point cloud 210 is designated as the reference point cloud. FIG. 5 illustrates an example of feature isolation performed by point cloud comparator 305 in accordance with some embodiments presented herein.

As shown in FIG. 5, second point cloud 220 may be aligned relative to first point cloud 210. Point cloud comparator 305 may isolate particular feature 230-2 in second point cloud 220 by locating (at 505) internal landmarks 510, 515, and 520 of first point cloud 210 and second point cloud 220 between the point cloud periphery and particular feature 230-2. In some embodiments, internal landmarks 510, 515, and 520 may include sets of point cloud data points that are at the exterior of point clouds 210 and 220 but closer to particular feature 230-2. In some embodiments, internal landmarks 510, 515, and 520 may include sets of point cloud data points within the interior of point clouds 210 and 220. Internal landmarks 510, 515, and 520, like external landmarks 410, 415, and 420, may correspond to a distinctive grouping or clustering of data points that form static or unique formations from which point cloud comparator 305 may determine the orientation, positioning, and/or layout of particular feature 130 in point clouds 210 and 220 (relative to the external landmarks and/or visual characteristics of point clouds 210 and 220). For example, external landmarks 410, 415, and 420 may correspond to a top stem of an imaged piece of fruit, internal landmarks 510, 515, and 520 may correspond to the core or center of the fruit, and point cloud comparator 305 may use these landmarks to locate a particular feature of the fruit. As another example, a decaying artifact may appear mostly uniform. However, point clouds 210 and 220 may capture distinct compositions or concentrations of elements, materials, or other matter at different parts of the artifact based on the non-positional data elements or visual characteristics of the data points, and point cloud comparator 305 may use the data points with the non-positional data elements for the distinct compositions or concentrations as landmarks from which to align point clouds 210 and 220, and from which to identify the same particular feature in point clouds 210 and 220. As another example, point clouds 210 and 220 may image a patient's intestines. The position, orientation, and portion of the intestines being scanned may change from first point cloud 210 to second point cloud 220. However, point cloud comparator 305 may identify sets of data points that represent distinctive blood vessel branching or formations as landmarks from which to align point clouds 210 and 220, and from which to identify the same particular feature in point clouds 210 and 220.

Figure 6:
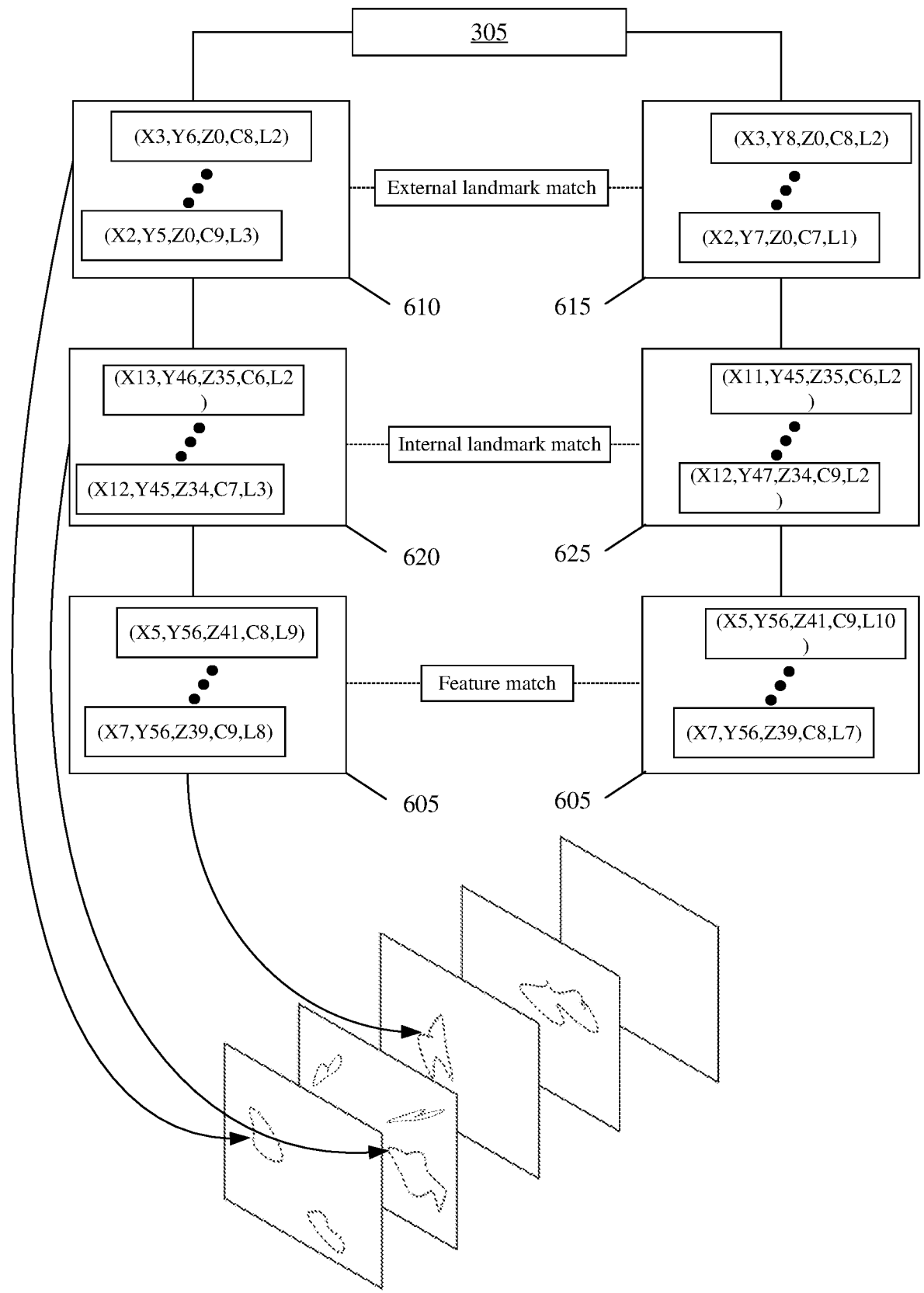
FIG. 6 illustrates an example of transitioning from an exterior set of landmarks to an interior set of landmarks in order to locate a particular feature in accordance with some embodiments presented herein.

FIG. 6 illustrates an example of transitioning from an exterior set of landmarks to an interior set of landmarks in order to locate particular feature 605 in accordance with some embodiments presented herein. In this figure, the point cloud data points for first point cloud 210 and second point cloud 220 may include x, y, and z positional data elements, and chrominance ("C") and luminance ("L") non-positional data elements. It should be apparent, that the data point may include other positional and non-positional data elements including data elements for representing power, temperature, thickness, density, etc.

As shown in FIG. 6, data point comparator 305 may locate particular feature 605 by gradually honing in on particular feature 605 via different sets of data points that are represent common landmarks of first point cloud 210 and second point cloud 220 and that lead to or can be used to identify particular feature 605. Specifically, data point comparator 305 may start and the periphery of point clouds 210 and 220, and may determine that first set of data points 610 for a particular external landmark of first point cloud 210 is within acceptable thresholds of second set of data points 615 for the same particular external landmark of second point cloud 220. Point cloud comparator 305 may then locate third set of data points 620 for a particular internal landmark of first point cloud 210 that is closer to particular feature 605 and within an interior of the imaged object and that is within acceptable thresholds of fourth set of data points 625 for the same particular internal landmark of second point cloud 220. From the particular internal landmark, point cloud comparator 305 may identify the different sets of data points that represent the same but modified particular feature 605 in first point cloud 210 and second point cloud 220.

In some embodiments, point cloud comparator 305 automatically define the internal and external landmarks for identifying particular feature 605 by performing an outward traversal from particular feature 605 in the reference point cloud. For instance, point cloud comparator 305 may locate the set of data points for particular feature 605 in first point cloud 210 or the reference point cloud. The set of data points for particular feature 605 may be tagged or otherwise differentiated in first point cloud 210 when first point cloud 210 serves as the reference point cloud. Point cloud comparator 305 may then scan outwards from particular feature 605 in first point cloud 210, and may identify clusters of data points that can serve as internal landmarks (e.g., set of data points 620) and external landmarks (e.g., set of data points 610) to particular feature 605. Here again, the landmarks can be unique or distinct sets of data points that can be differentiated from other data points of the reference point cloud. For instance, a cluster with a high concentration of data points, a cluster of data points in a particular shape or orientation, and/or a cluster of data point with specific visual characteristics can serve as landmarks. More specifically, a cluster of data points with a specific coloring, luminosity, and/or chrominance that is different from the coloring, luminosity, and/or chrominance of other neighboring data points can be selected as a landmark. Point cloud comparator 305 may determine distances between each internal landmark and particular feature 605, and/or between each internal landmark and one or more landmarks at the periphery of the point cloud that were used in aligning the point clouds.

After determining the landmarks and their positioning within first point cloud 210, point cloud comparator 305 may scan the data points of second data point 220 in order to locate one or more of the same internal landmarks in second point cloud 220. A matching landmark may include a set of data points within second point cloud 220 that have positional and/or non-positional data elements within a threshold of the positional and/or non-positional data elements for the set of data points that represent the same internal landmark in first point cloud 210.

By traversing the same landmarks in the different point clouds 210 and 220, point cloud comparator 220 may isolate particular feature 605 in second point cloud 220 without having to scan or match each and every data point in point clouds 210 and 220. In particular, point cloud comparator 305 may identify internal landmarks that are closest to the landmarks at the outer edges, and may continue inwards until one or more sets of data points corresponding to the internal landmarks that are closest to particular feature 605 are identified in second point cloud 220. In this manner, point cloud comparator 305 may scan smaller regions of second point cloud 220 to move closer to isolating particular feature 605. In some embodiments, point cloud comparator 305 may reference distance information between the internal landmarks from first point cloud 210 in determining the next set of data points from second point cloud 220 to scan in order to locate the next closer landmark to particular feature 605.

From the nearest landmarks to particular feature 605, point cloud comparator 305 may isolate the data points in second point cloud 220 that correspond to particular feature 605. In particular, point cloud comparator 305 may determine a distance and/or vector from data points of each closest landmark to one or more data points at a center of particular feature 605 in the reference point cloud or first point cloud 210. Point cloud comparator 305 may then shift the same distance and in the same direction from each matching landmark found in second point cloud 220 to search for data points in second point cloud 605 with positional and non-positional data elements that are within a threshold of the data points forming particular feature 605 in first point cloud 210 and that represent the data points for particular feature 605 in second point cloud 220. Point cloud comparator 305 need not find an exact match for each data point of particular feature 605 from first point cloud 210 in second point cloud 220. Rather, point cloud comparator 305 may identify particular feature 605 in second point cloud 220 based on a set of data points that have the same or similar properties as data points representing particular feature 605 in first point cloud 210. For instance, a foreign organism (e.g., the particular feature) within a host may change size, shape, and/or position from first point cloud 210 to second point cloud 220, but the general size, shape, and/or position of the foreign organism (e.g., the particular feature) may be similar. Moreover, the visual characteristics (e.g., luminosity, chrominance, hue, saturation, coloring, etc.) of the data points that differentiate the foreign organism from the host may be similar in the data points of second point cloud 220 that image the foreign organism.

Isolating particular feature 605 in second point cloud 220 may therefore include point cloud comparator 305 automatically and programmatically selecting a set of data points that represent particular feature 605 in second point cloud 220 based on a traversal of similar landmarks between the reference first point cloud 210 and second point cloud 220, and based on the matching of data points with similar visual characteristics as particular feature 605 in the area of particular feature 605 in both first point cloud 210 and second point cloud 220. Once first and second point clouds 210 and 220 are aligned and particular feature 605 is isolated in both, point cloud comparator 305 may compare the positional and non-positional data elements of the data points for particular feature 605 in each point cloud 210 and 220. From the comparison, point cloud comparator 305 may detect and measure variances that quantify the changes to particular feature 605 in the time between first point cloud 210 and second point cloud 220 are generated.

Figure 7:
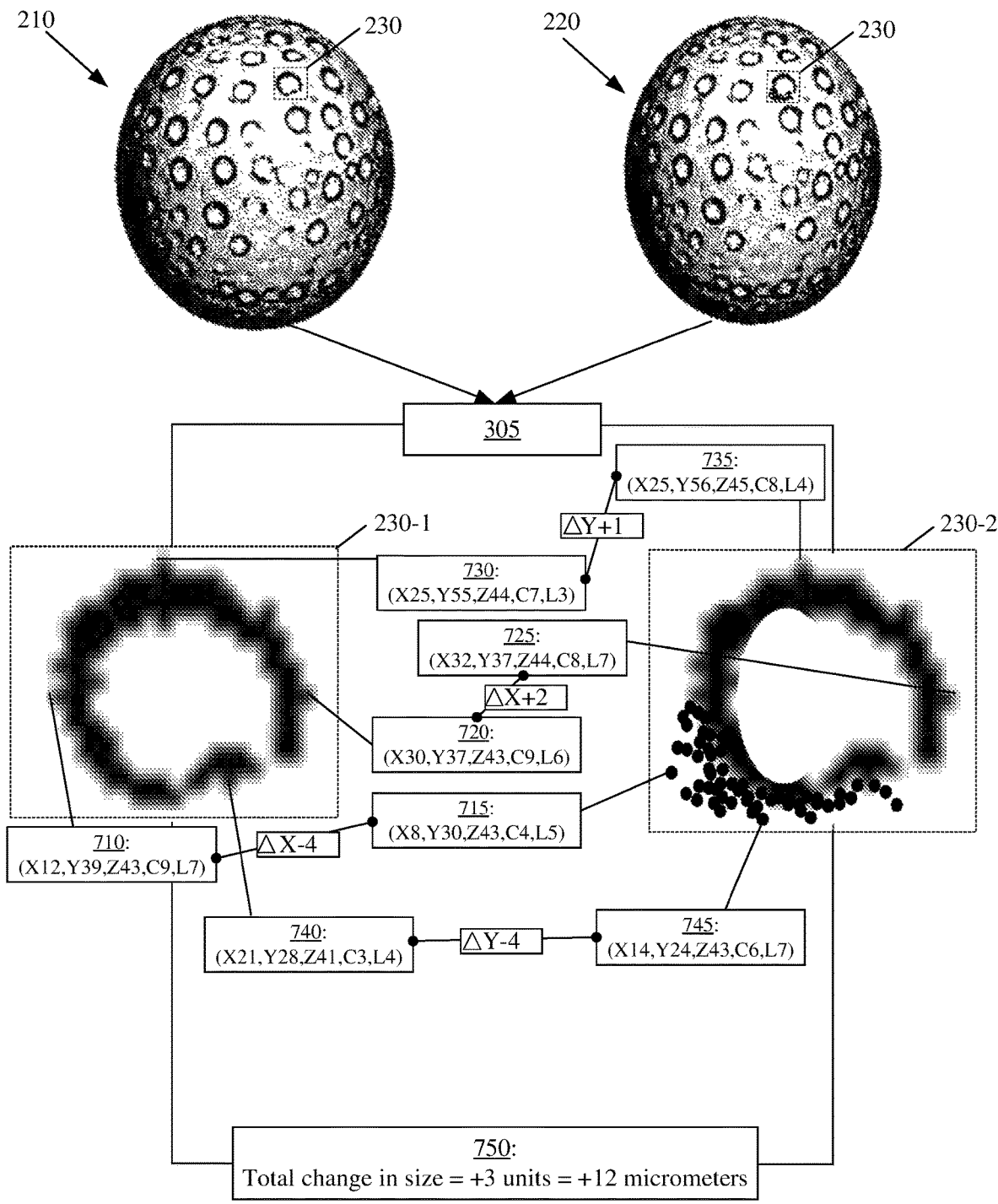
FIG. 7 illustrates an example of the point cloud comparator quantifying variance by detecting and measuring change that occurs to a particular feature over time as captured using different point clouds in accordance with some embodiments presented herein.

FIG. 7 illustrates an example of point cloud comparator 305 quantifying variance by detecting and measuring change that occurs to particular feature 230 over time as captured using different point clouds 210 and 220 in accordance with some embodiments presented herein. Point cloud comparator 305 may detect the data points that form particular feature 230 in first point cloud 210 and second point cloud 220. For instance, point cloud comparator 305 may detect sets of data points with similar landmarks including similar clustering, concentration, placement, positioning, shape, size, visual characteristics (e.g., red, green, blue, chrominance, luminance, etc.), and/or other data points with positional and non-positional data elements within a threshold of one another.

Point cloud comparator 305 may compare the sets of data points to determine the size, thickness, density, and shape of particular 230 in each point cloud 210 and 220 based on the positional data elements from the sets of data points. Point cloud comparator 305 may determine if the particular feature has increased or decreased in size, changed thickness, changed density, and/or changed shape based on the positioning and/or distance separating the data points at the periphery of particular feature 230 in each of first point cloud 210 and second point cloud 220, and may quantify the change by measuring the positional change for particular feature 230 data points in first point cloud 210 and second point cloud 220. For instance, point cloud comparator 305 may compare the positional data elements for leftmost data points 710 and 715 of particular feature 230 in first cloud 210 and second point cloud 220, rightmost data points 720 and 725, topmost data points 730 and 735, and/or bottommost data points 740 and 745 to determine (at 750) that particular feature 230 has increased in size by a specified number of units (e.g., increase of 3 units) or by a specific distance measurement that is calculated from the positional differences and the units represented by each positional data element. In some embodiments, point cloud comparator 305 may account for the frontmost and/or backmost data points (e.g., data points with smallest z-coordinate and largest z-coordinate) in each point cloud 210 and 220.

In some embodiments, point cloud comparator 305 may compare all data points for particular feature 230-1 of first point cloud 210 to the data points for particular feature 230-2 of second point cloud 220 for any variance. In some other embodiments, point cloud comparator 305 may compare a sampled subset of data points (e.g., data points for certain landmarks) for particular feature 230 of first point cloud 210 and second point cloud 220. For instance, point cloud comparator 305 may compare the data points for particular feature 230 at the outer most edges, at the center, and/or data points in specific clusters of particular feature 230.

Point cloud comparator 305 may obtain point cloud resolution information from the files that store first point cloud 210 and second point cloud 220, and may determine that each unit corresponds to 4 micrometers. Accordingly, point cloud comparator 305 may compute that the particular feature has increased 3 units or 12 micrometers in size from first point cloud 210 to second point cloud 220.

In some embodiments, point cloud comparator 305 may compute the surface area or volume of the particular feature based on the positional data elements, and may use the surface area or volume computation to quantify the change in size or shape. For instance, point cloud comparator 305 may detect that the outer edges of a particular feature (e.g., feature data points with minimum and maximum x, y, and z coordinates), may generate a bounding cube from the outer edges of the particular feature, and may compute the volume of the cube to determine the size of the particular feature. Other computations, including average mean distance, standard deviation, etc., may be used to further quantify the change in size and/or shape of particular feature 230.

Point cloud comparator 305 may supplement the size or shape measurements, or may derive secondary size or shape measurements, based on the non-positional data elements or visual characteristics of the data points representing particular feature 230 in first point cloud 210 and second point cloud 220. For instance, changes in chrominance, luminosity, coloring, and/or visual characteristics of the data points may map to changes in size or shape of particular feature 230.

Point cloud comparator 305 may detect and/or measure changes in particular feature 230 density based on a change in the concentration (e.g., average distance between data points) or number of data points that represent particular feature 230 in first point cloud 210 and second point cloud 220. For instance, a higher concentration of data points may be indicative of greater mass or an increase in thickness of particular feature 230.

Point cloud comparator 305 may also measure changes in particular feature 230 density based on changes in the non-positional data elements or visual characteristics of the data points. For instance, point cloud comparator 305 may determine that a set of data points in the same location and with the same concentration have a greater density in first point cloud 210 than in second point cloud 220 based on the differences in the luminosity, chrominance, coloring, and/or other visual features of the set of data points.

In some embodiments, point cloud comparator 305 may detect and/or measure decay in particular feature 230 based on changes in the positional and non-positional data elements of the particular feature data points. In an agricultural context, fewer data points for particular feature 230 in second point cloud 220 than in first point cloud 210 may indicate decay, rot, or deterioration. Data points with less reflectivity in second point cloud 220 than in first point cloud 210 may also indicate decay, rot, or deterioration of particular feature 230. In a manufacturing context, fewer data points for particular feature 230 in second point cloud 220 than in first point cloud 210 may indicate less thickness, density, or another quality control or manufacturing issue.

Conversely, more data points for particular feature 230 in second point cloud 220 than in first point 210 may indicate growth, and data points with greater reflectivity and/or different coloring may indicate health of particular feature 230. In a medical context, fewer data points for particular feature 230 in second point cloud 220 than in first point cloud 210 may indicate cancer remission, and data points with different visual characteristics may indicate viral spread, inflammation, and/or disease. In a art context, fewer or a different arrangement of data points for particular 230 in second point cloud 220 than in first point cloud 210 may be used to spot a copy and/or forgery of an original piece of art.

In any case, point cloud comparator 305 may quantify the changes based on the detected changes in the positional and/or non-positional data elements for data points of particular feature 230 from different point clouds 210 and 220. Depending on the resolution of the imaging equipment used to capture first point cloud 210 and second point cloud 220, each data point positional data element may map to a specific unit of length, distance, and/or other measure.

Figure 8:
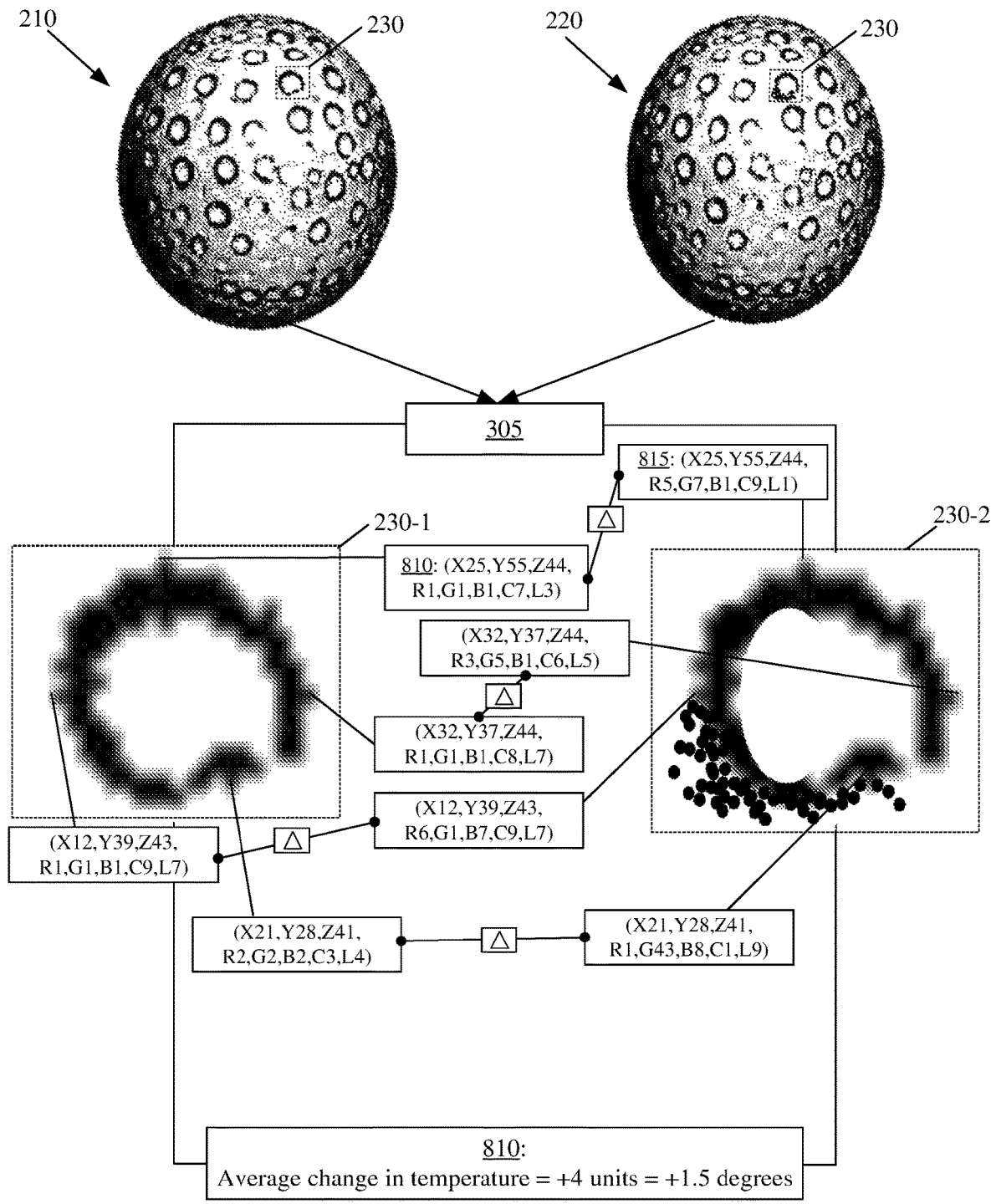
FIG. 8 illustrates an example of the point cloud comparator measuring a change in the particular feature size based on detected variance in the visual characteristics of the particular feature data points in accordance with some embodiments presented herein.

FIG. 8 illustrates an example of point cloud comparator 305 measuring a change in the particular feature size based on detected variance in the visual characteristics of the particular feature data points in accordance with some embodiments presented herein. As shown in FIG. 8, there may no change to the positioning of the data points from particular feature 230 in first point cloud 210 and second point cloud 220. However, the visual characteristics of the data points may have changed. For instance, point cloud comparator 305 may detect changes to the red, green, blue, luminosity, chrominance, hue, saturation, brightness, reflectivity, and/or other non-positional data elements of the data points. As a specific example, point cloud comparator 305 may detect that the positional data elements for data points 810 and 815 have not changed, but that the red, green, chrominance, and luminance data elements have changed for the same data point of particular feature 230 in first point cloud 210 and second point cloud 220.

Point cloud comparator 305 may map (at 820) the detected differences in visual characteristics to changes in temperature, health, quality measurements, density, composition, mass, strength, decay, rot, inflammation, infection, size, growth, and/or other properties of particular feature 230. In mapping (at 820) the detected differences, point cloud comparator 305 may quantify each such detected change to a desired range or scale of values. For instance, point cloud comparator 305 may map (at 820) detected changes in visual characteristics to a reduced temperature that may indicate that an infection, disease, or other foreign organism has been eliminated from particular feature 230, or to an increase in temperature that may indicate a worsening of the infection, disease, or other foreign organism.

Figure 9:
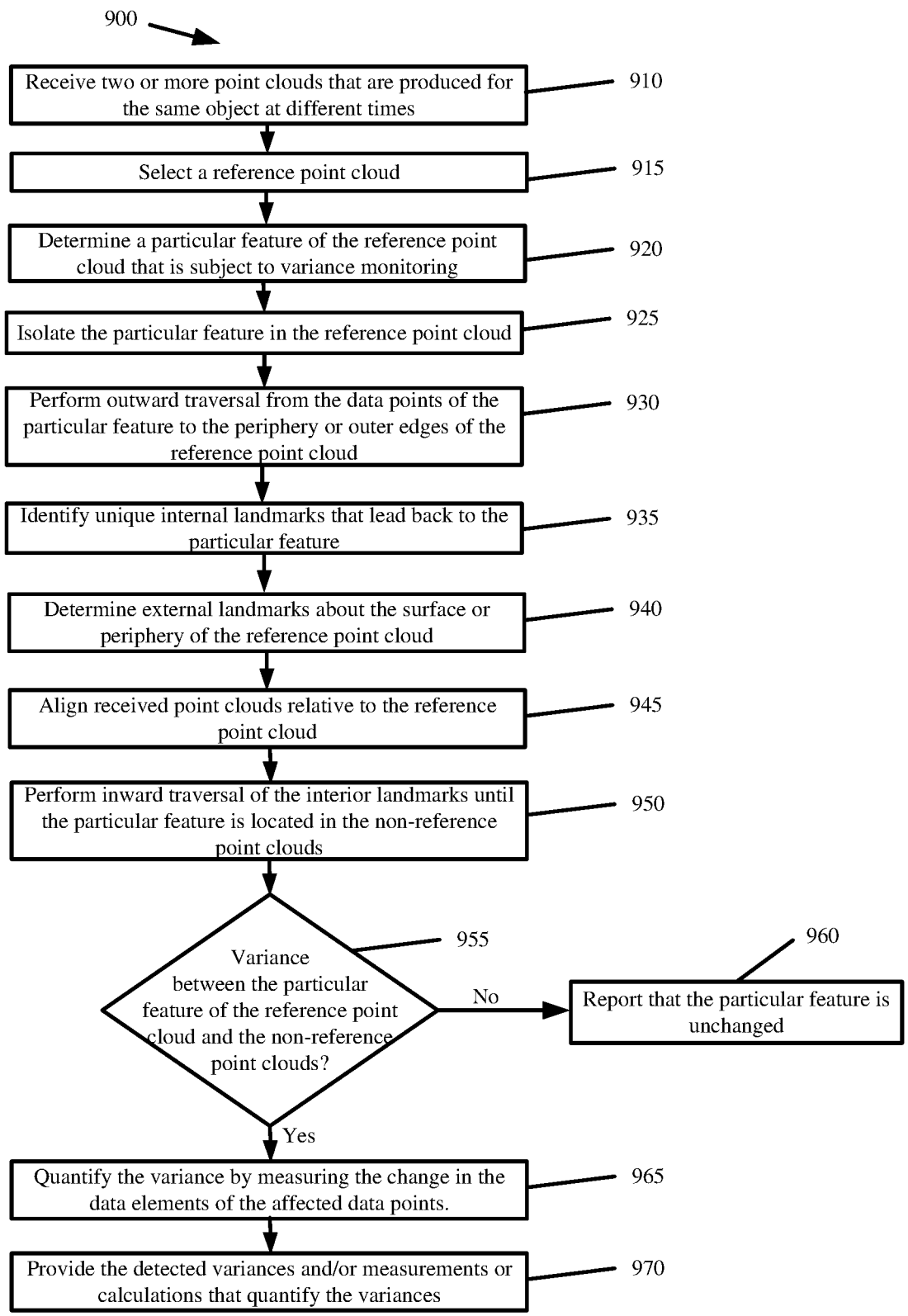
FIG. 9 presents a process for automatically detecting and measuring variance using point clouds in accordance with some embodiments presented herein.

FIG. 9 presents a process 900 for automatically detecting and measuring variance using point clouds in accordance with some embodiments presented herein. Process 900 may be implemented by point cloud comparator 305.

Process 900 may include receiving (at 910) two or more point clouds that are produced for the same object at different times. For instance, a first point cloud may be generated at a first time and a second point cloud may be generated at a second time. The point clouds may provide 3D images of agricultural products, architectural artifacts, patient medical scans, images of living organisms, and/or other objects.

Process 900 may include selecting (at 915) one of the two or more point clouds as a reference point cloud. The selection of the reference point cloud may be based on point cloud timestamps, development or absence of one or more features, or other automatic or manual selection.

Process 900 may include determining (at 920) a particular feature of the reference point cloud that is subject to variance monitoring. The particular feature may correspond to a specific subset of data points in the reference point cloud, and the specific subset of data points may vary by some degree to other neighboring data points in the reference point cloud. In some embodiments, the particular feature may represent a foreign body, virus, disease, rot, decay, growth, abnormality, and/or another part of the point cloud object where change is of particular interest.

In some embodiments, point cloud comparator 305 may automatically determine (at 920) the particular feature within the reference point cloud in response to input. For instance, the input may specify identification of a cancerous growth as the particular feature. Point cloud comparator 305 may use artificial intelligence and/or machine learning to examine a baseline set of point clouds where cancerous growths are identified. Point cloud comparator 305 may determine data point formations (e.g., positional data elements) and visual characteristics (e.g., non-positional data elements) that are representative of different cancerous growths, and may automatically identify the particular feature in the reference point cloud based on the artificial intelligence and/or machine learning.

In some other embodiments, point cloud comparator 305 may determine (at 920) the particular feature within the reference point cloud based on a direct identification or selection of the particular feature in the reference point cloud by a user or another machine. For instance, a user may manually examine the reference point cloud, may select the specific subset of data points that represent the particular feature, and may provide the selection to point cloud comparator 305.

Process 900 may include isolating (at 925) the particular feature in the reference point cloud. Isolating (at 925) the particular feature may include comparing positional and non-positional data elements of the specific subset of data points, that form the particular feature in the reference point cloud, to the same data elements of neighboring data points. From the comparison, point cloud comparator 305 may identify distinctive positional data (e.g., clustering, arrangements, positional patterns, densities, concentrations, landmarks, etc.) from which the particular feature can be differentiated from other data points and/or features of the reference point cloud. From the comparison, point cloud comparator 305 may also identify distinctive visual characteristics that differentiate the specific subset of data points for the particular feature from other data points and/or features of the reference point cloud. For instance, point cloud comparator 305 may isolate (at 925) the specific subset of data points for the particular feature based on distinct coloring, luminance, chrominance, and/or other visual characteristics of the particular feature data points.

Process 900 may include performing (at 930) an outward traversal from the data points of the particular feature to the periphery or outer edges of the reference point cloud, and identifying (at 935) unique internal or interior landmarks that lead back to the particular feature. Point cloud comparator 305 may inspect the data points of the reference point cloud in order to identify additional sets of data points that distinctly identify the internal or interior landmarks.

Process 900 may include determining (at 940) one or more external or exterior landmarks about the surface or periphery of the reference point cloud. In some embodiments, the object that is imaged by the two or more point clouds may have an irregular shape or irregularities about the exterior surface, and the external or exterior landmarks may correspond to the data points for the irregularities or irregular shapes.

Process 900 may include aligning (at 945) the other received (at 910) point clouds (e.g., the non-reference point clouds) relative to the reference point cloud. The alignment (at 945) may include locating the external or exterior landmarks of the non-reference point clouds by identifying data points about the exterior surface or periphery of the non-reference point clouds that have positional and/or non-positional data elements within a threshold of the data point data elements for the external or exterior landmarks of the reference point cloud. The alignment (at 945) may further include rotating, reorienting, shifting, and/or otherwise repositioning the other point clouds so that the external or exterior landmarks become aligned with those of the reference point cloud.

Process 900 may include performing (at 950) an inward traversal of the internal or interior landmarks until the particular feature is located in the non-reference point clouds. Here again, point cloud comparator 305 may identify data point data elements of the non-reference point clouds with values that are within one or more thresholds of the values for the data point data elements for the internal or interior landmarks and the particular feature of the reference point cloud. In this manner, point cloud comparator 305 may accurately locate the same particular feature in different point clouds despite movement, shifting, or change occurring to one or more of the landmarks or the particular feature in the different point clouds. Other techniques may be used to isolate the same particular feature, with or without modification, in a 3D array of data points from different point clouds.

Process 900 may include detecting (at 955) variance between the particular feature of the reference point cloud and the non-reference point clouds for the same object. Detecting (at 955) the variance may include comparing the number of data points and the positional information between the sets of data points of the particular feature in the different point clouds to determine if the particular feature has changed shape, size, density, position, and/or other physical dimensions. In some embodiments, point cloud comparator 305 may detect a variance when the differences in positional information for the particular feature of two different point clouds exceed a threshold. For instance, no variance may be detected if there is less than a 5% difference in the number of data points that image the particular feature in two or more point clouds, or if the positional change in the size, shape, density, and/or position of the data points is less than 10%. Detecting (at 955) the variance may also include comparing the visual characteristics or non-positional data elements between the sets of data points of the particular feature in the different point clouds to determine if the particular feature has changed. In some embodiments, point cloud comparator 305 may detect a variance when the differences in visual characteristics of the sets of data points for the particular feature of two different point clouds exceed a threshold. For instance, no variance may be detected if there is less than a 10% difference in the coloring, chrominance, luminance, and/or other visual characteristic data elements. However, a difference greater than 10% in the visual characteristics may indicate a change in inflammation, health, decay, strength, temperature, etc.

In response to detecting (at 955—No) no variance, process 900 may include reporting (at 960) that the particular feature is unchanged or that the change to the particular feature is within acceptable tolerances or thresholds. In some embodiments, point cloud comparator 305 may provide a diagnostic that the object or the particular feature of the object remains in a desired state. In some embodiments, the point clouds may be stored as a baseline against which subsequently produced point clouds of the same object may be compared.

In response to detecting (at 955—Yes) variance, process 900 may include quantifying (at 965) the variance by measuring the change in the data elements of the affected data points. Quantifying (at 965) the variance may include computing the delta or difference in the values of the data point data elements, and/or mapping the resulting delta or difference to one or more measurable values. For instance, a delta in the positional coordinates for the data points at the periphery of the particular feature in different point clouds may be mapped to a distance measurement with units (e.g., micrometer, millimeter, centimeter, etc.) that quantify an increase or decrease in size of the particular feature. Similarly, a delta in visual characteristics may be mapped to a temperature change, an amount of inflammation, an infection percentage, and/or measures. In some embodiments, point cloud comparator 305 may use more robust calculations (e.g., means, medians, averages, volume computations, standard deviations, etc.) to quantify (at 965) and map the changes in the data point data elements to actual measures. Process 900 may include providing (at 970) or outputting the detected variances and/or measurements or calculations that quantify the variances via a display, in a file, or as metadata of the point cloud. In some embodiments, point cloud comparator 305 may provide a diagnostic that the object or the particular feature of the object has deviated from a desired state, and may further suggest actions for correcting the change.

In this manner, point cloud comparator 305 may accurately detect and measure microscopic or subtle changes to specific parts of an object without human bias or subjectivity. Moreover, the point clouds allow point cloud comparator 305 to detect and measure these changes on the object exterior or periphery as well as within the object interior.

The results that are generated by point cloud comparator 305 may be reproducible and exact because point cloud comparator 305 compares the same fixed values from individual data points or subsets of data points for the same feature, whereas the same human diagnostician may have a different opinion each time the point clouds or images are compared.

In some embodiments, point cloud comparator 305 may correspond to one or more devices with processors and/or specialized hardware for detecting and measuring feature variance between two or more point clouds and/or other files. The devices may be on-premises or may be remotely accessed from the "cloud" via a network. Accordingly, point cloud comparator 305 may include a computing device, such as a desktop computer, a network accessible server, a consumer or business appliance, a "smart" display, a set-top box, or another device that can be used to access two or more point clouds and/or perform the comparisons.

In some embodiments, point cloud comparator 305 may be a software component or service that is executed by one or more processors. In some such embodiments, point cloud comparator 305 may be a centralized service that can be accessed and performed on a single computing node, or may be a distributed service in which resources of two or more computing nodes may be used to perform the variance detection and/or measurement.

Figure 10:
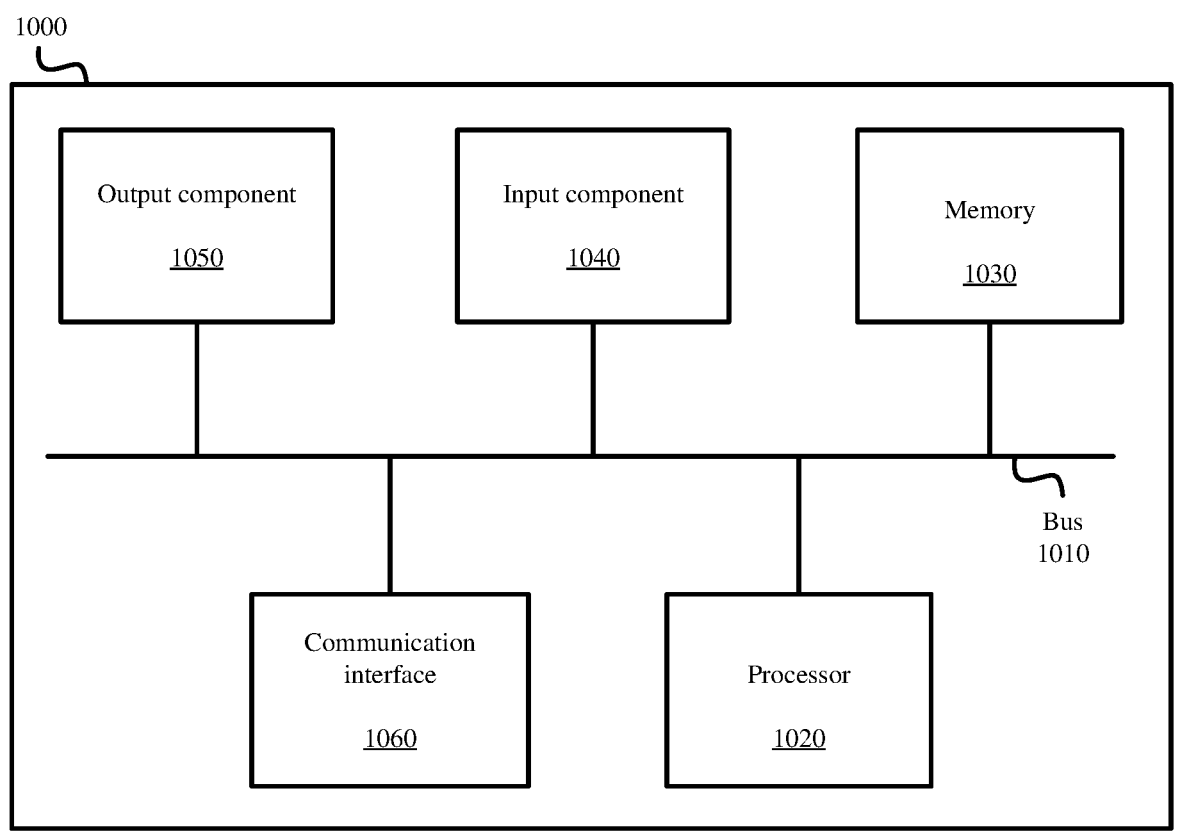
FIG. 10 illustrates example components of one or more devices, according to one or more embodiments described herein.

FIG. 10 is a diagram of example components of device 1000. Device 1000 may be used to implement one or more of the devices or systems described above (e.g., point cloud comparator 305). Device 1000 may include bus 1010, processor 1020, memory 1030, input component 1040, output component 1050, and communication interface 1060. In another implementation, device 1000 may include additional, fewer, different, or differently arranged components.

Bus 1010 may include one or more communication paths that permit communication among the components of device 1000. Processor 1020 may include a processor, microprocessor, or processing logic that may interpret and execute instructions. Memory 1030 may include any type of dynamic storage device that may store information and instructions for execution by processor 1020, and/or any type of non-volatile storage device that may store information for use by processor 1020.

Input component 1040 may include a mechanism that permits an operator to input information to device 1000, such as a keyboard, a keypad, a button, a switch, etc. Output component 1050 may include a mechanism that outputs information to the operator, such as a display (e.g., 2D, 3D, virtual reality, augmented reality, holographic, etc.), a heads-up display, a projector, a speaker, one or more light emitting diodes ("LEDs"), etc.

Communication interface 1060 may include any transceiver-like mechanism that enables device 1000 to communicate with other devices and/or systems. For example, communication interface 1060 may include an Ethernet interface, an optical interface, a coaxial interface, or the like. Communication interface 1060 may include a wireless communication device, such as an infrared ("IR") receiver, a Bluetooth® radio, or the like. The wireless communication device may be coupled to an external device, such as a remote control, a wireless keyboard, a mobile telephone, etc. In some embodiments, device 1000 may include more than one communication interface 1060. For instance, device 1000 may include an optical interface and an Ethernet interface.

Device 1000 may perform certain operations relating to one or more processes described above. Device 1000 may perform these operations in response to processor 1020 executing software instructions stored in a computer-readable medium, such as memory 1030. A computer-readable medium may be defined as a non-transitory memory device. A memory device may include space within a single physical memory device or spread across multiple physical memory devices. The software instructions may be read into memory 1030 from another computer-readable medium or from another device. The software instructions stored in memory 1030 may cause processor 1020 to perform processes described herein. Alternatively, hardwired circuitry may be used in place of or in combination with software instructions to implement processes described herein. Thus, implementations described herein are not limited to any specific combination of hardware circuitry and software.

The foregoing description of implementations provides illustration and description, but is not intended to be exhaustive or to limit the possible implementations to the precise form disclosed. Modifications and variations are possible in light of the above disclosure or may be acquired from practice of the implementations.

The actual software code or specialized control hardware used to implement an embodiment is not limiting of the embodiment. Thus, the operation and behavior of the embodiment has been described without reference to the specific software code, it being understood that software and control hardware may be designed based on the description herein.

For example, while series of messages, blocks, and/or signals have been described with regard to some of the above figures, the order of the messages, blocks, and/or signals may be modified in other implementations. Further, non-dependent blocks and/or signals may be performed in parallel. Additionally, while the figures have been described in the context of particular devices performing particular acts, in practice, one or more other devices may perform some or all of these acts in lieu of, or in addition to, the above-mentioned devices.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

Further, while certain connections or devices are shown, in practice, additional, fewer, or different, connections or devices may be used. Furthermore, while various devices and networks are shown separately, in practice, the functionality of multiple devices may be performed by a single device, or the functionality of one device may be performed by multiple devices. Further, while some devices are shown as communicating with a network, some such devices may be incorporated, in whole or in part, as a part of the network.

To the extent the aforementioned embodiments collect, store or employ personal information provided by individuals, it should be understood that such information shall be used in accordance with all applicable laws concerning protection of personal information. Additionally, the collection, storage and use of such information may be subject to consent of the individual to such activity, for example, through well-known "opt-in" or "opt-out" processes as may be appropriate for the situation and type of information. Storage and use of personal information may be in an appropriately secure manner reflective of the type of information, for example, through various encryption and anonymization techniques for particularly sensitive information.

Some implementations described herein may be described in conjunction with thresholds. The term "greater than" (or similar terms), as used herein to describe a relationship of a value to a threshold, may be used interchangeably with the term "greater than or equal to" (or similar terms). Similarly, the term "less than" (or similar terms), as used herein to describe a relationship of a value to a threshold, may be used interchangeably with the term "less than or equal to" (or similar terms). As used herein, "exceeding" a threshold (or similar terms) may be used interchangeably with "being greater than a threshold," "being greater than or equal to a threshold," "being less than a threshold," "being less than or equal to a threshold," or other similar terms, depending on the context in which the threshold is used.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items, and may be used interchangeably with the phrase "one or more." Where only one item is intended, the terms "one," "single," "only," or similar language is used. Further, the phrase "based on" is intended to mean "based, at least in part, on" unless explicitly stated otherwise.

What is claimed is:

1. A method comprising:
    receiving at least first and second point clouds, each of the first and second point clouds comprising a plurality of data points that collectively produce a three-dimensional ("3D") image of a common object that is captured at different times, each data point of the plurality of data points comprising positional values that define a position of the data point in 3D space, and visual characteristic values that define visual characteristics of the data point;
    isolating a first set of the plurality of data points from the first point cloud that represent a particular feature of the common object at a first time;
    isolating a second set of the plurality of data points from the second point cloud that represent the particular feature of the common object at a different second time, wherein said isolating the second set of data points comprises:
        matching, by a threshold, the positional values and the visual characteristic values for a first subset of the second set of data points from the second point cloud to the positional values and the visual characteristic values for a corresponding first subset of the first set of data points from the first point cloud;
    detecting a variance between the positional values and the visual characteristic values for a second subset of the second set of data points and the positional values and the visual characteristic values for a corresponding second subset of the first set of data points; and
    quantifying a change occurring to the particular feature between the first time and the second time by converting the variance to a first unit of measure, wherein the first unit of measure differs from at least a second unit of measure, that is used in defining the positional values, and at least a third unit of measure, that is used in defining the visual characteristic values.

2. The method of claim 1, wherein isolating the first set of data points comprises:
    determining different subsets of the plurality of data points from the first point cloud that distinctively identify different landmarks of the common object that lead to the particular feature.

3. The method of claim 2,
    wherein each of the different landmarks corresponds to a unique clustering of a subset of data points that is differentiated from neighboring data points of the first point cloud, and
    wherein the different landmarks comprise at least one subset of data points about the exterior or periphery of the first point cloud, and another subset of data points within the interior of the first point cloud.

4. The method of claim 2, wherein isolating the second set of data points further comprises:
    selecting the second set of data points from the plurality of data points of the second point cloud by traversing different subsets of the plurality of data points from the second point cloud having the positional values or the visual characteristic values that match by a threshold to the positional values or the visual characteristic values of the subsets of data points from the first point cloud for each of the different landmarks leading to the particular feature.

5. The method of claim 1 further comprising:
    aligning the second point cloud relative to the first point cloud prior to isolating the second set of data points.

6. The method of claim 5, wherein aligning the second point cloud comprises:
correcting for one or more rotations, shifts, skew, and distortions that offset the plurality of data points of the second point cloud from the plurality of data points of the first point cloud.

7. The method of claim 5, wherein aligning the second point cloud comprises:
detecting clusters of data points about an exterior or periphery of the second point cloud that correspond to and are offset from clusters of data points about an exterior or periphery of the first point cloud by at least one delta; and
reducing the offset between the clusters of data points about the exterior or periphery of the second point cloud and the clusters of data points about the exterior or periphery of the first point cloud by modifying values of the plurality of data points of the second point cloud according to the at least one delta.

8. The method of claim 1, wherein quantifying the change comprises:
calculating a change in size or shape of the particular feature based on the variance and conversion of the variance to the first unit of measure.

9. The method of claim 1, wherein quantifying the change comprises:
determining an increase to a size of the particular feature based on the variance corresponding to an increase in the number of data points from the first set of data points to the second set of data points.

10. The method of claim 1, wherein quantifying the change comprises:
calculating a temperature change based on the variance and the first unit of measure corresponding to a temperature measure.

11. The method of claim 1, wherein quantifying the change comprises:
measuring a temperature change of the particular feature based on a change between the visual characteristics of the first set of data points and the visual characteristics of the second set of data points.

12. The method of claim 1, wherein quantifying the change comprises:
measuring an amount of decay or deterioration in the particular feature based on the variance corresponding to a reduction in a number of data points from the first set of data points to the second set of data points, or based on a change to the visual characteristics of the second set of data points from the visual characteristics of the first set of data points.

13. The method of claim 1, wherein quantifying the change comprises:
determining a change in density of the particular feature based on one or more of a change in positioning between the first set of data points and the second set of data points and a change between the visual characteristics of the first set of data points and the visual characteristics of the second set of data points.

14. The method of claim 1, wherein quantifying the change comprises:
measuring growth of a living organism based on the variance and the first unit of measure corresponding to a distance measure.

15. The method of claim 1, wherein quantifying the change comprises:
determining spread of a foreign body within a living organism based on the variance and conversion of the variance to a distance measure, wherein the foreign body may comprise a virus, disease, bacteria, infection, or abnormal growth.

16. The method of claim 1, wherein quantifying the change comprises:
measuring an amount of inflammation to the particular feature based on the variance and the first unit of measure corresponding to an inflammation measure.

17. The method of claim 1, wherein quantifying the change comprises:
measuring strength of the particular feature within the common object based on the variance and the first unit of measure corresponding to a density measure.

18. The method of claim 1, wherein quantifying the change comprises:
measuring health of the particular feature within the common object based on the variance and the first unit of measure corresponding to a health measure.

19. A device comprising:
one or more processors configured to:
receive at least first and second point clouds, each of the first and second point clouds comprising a plurality of data points that collectively produce a three-dimensional ("3D") image of a common object that is captured at different times, each data point of the plurality of data points comprising positional values that define a position of the data point in 3D space, and visual characteristic values that define visual characteristics of the data point;
isolate a first set of the plurality of data points from the first point cloud that represent a particular feature of the common object at a first time;
isolate a second set of the plurality of data points from the second point cloud that represent the particular feature of the common object at a different second time, wherein said isolating the second set of data points comprises:
matching, by a threshold, the positional values and the visual characteristic values for a first subset of the second set of data points from the second point cloud to the positional values and the visual characteristic values for a corresponding first subset of the first set of data points from the first point cloud;
detect a variance between the positional values and the visual characteristic values for a second subset of the second set of data points and the positional values and the visual characteristic values for a corresponding second subset of the first set of data points; and
quantify a change occurring to the particular feature between the first time and the second time by converting the variance to a first unit of measure, wherein the first unit of measure differs from at least a second unit of measure, that is used in defining the positional values, and at least a third unit of measure, that is used in defining the visual characteristic values.

20. A non-transitory computer-readable medium, storing a plurality of processor-executable instructions to:
receive at least first and second point clouds, each of the first and second point clouds comprising a plurality of data points that collectively produce a three-dimensional ("3D") image of a common object that is captured at different times, each data point of the plurality of data points comprising positional values that define a position of the data point in 3D space, and visual characteristic values that define visual characteristics of the data point;

isolate a first set of the plurality of data points from the first point cloud that represent a particular feature of the common object at a first time;

isolate a second set of the plurality of data points from the second point cloud that represent the particular feature of the common object at a different second time, wherein said isolating the second set of data points comprises:

matching, by a threshold, the positional values and the visual characteristic values for a first subset of the second set of data points from the second point cloud to the positional values and the visual characteristic values for a corresponding first subset of the first set of data points from the first point cloud;

detect a variance between the positional values and the visual characteristic values for a second subset of the second set of data points and the positional values and the visual characteristic values for a corresponding second subset of the first set of data points; and quantify a change occurring to the particular feature between the first time and the second time by converting the variance to a first unit of measure, wherein the first unit of measure differs from at least a second unit of measure, that is used in defining the positional values, and at least a third unit of measure, that is used in defining the visual characteristic values.

* * * * *